(12) United States Patent
Rava et al.

(10) Patent No.: US 6,720,149 B1
(45) Date of Patent: Apr. 13, 2004

(54) METHODS FOR CONCURRENTLY PROCESSING MULTIPLE BIOLOGICAL CHIP ASSAYS

(75) Inventors: Richard P. Rava, San Jose, CA (US); Stephen P. A. Fodor, Palo Alto, CA (US); Mark Trulson, San Jose, CA (US); Vernon A. Norviel, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 10/157,252

(22) Filed: May 28, 2002

Related U.S. Application Data

(63) Continuation of application No. 09/247,430, filed on Feb. 10, 1999, now abandoned, which is a continuation of application No. 08/630,051, filed on Apr. 9, 1996, now Pat. No. 5,874,219, which is a continuation of application No. 08/476,850, filed on Jun. 7, 1995, now Pat. No. 5,545,531.

(51) Int. Cl.$^7$ .............................. C12Q 1/68; C12M 1/34; C07H 21/04
(52) U.S. Cl. ........................ 435/6; 435/288.4; 536/23.1; 536/24.3
(58) Field of Search ........................ 435/6, 91.2, 288.4, 435/DIG. 49, 24.33, 5, 7.1, 7.9; 536/23.1, 24.3, 24.37, 33

(56) References Cited

U.S. PATENT DOCUMENTS

| | | | |
|---|---|---|---|
| 5,002,889 A | * | 3/1991 | Klein ......................... 435/284 |
| 5,143,854 A | | 9/1992 | Pirrung et al. |
| 5,196,305 A | | 3/1993 | Findlay et al. |
| 5,288,514 A | | 2/1994 | Ellman |
| 5,348,855 A | | 9/1994 | Dattagupta et al. |
| 5,382,512 A | | 1/1995 | Smethers et al. |
| 5,384,261 A | | 1/1995 | Winkler et al. |
| 5,424,186 A | * | 6/1995 | Fodor et al. ................... 435/6 |
| 5,489,678 A | | 2/1996 | Fodor et al. |
| 5,538,857 A | | 7/1996 | Rosenthal et al. |
| 5,545,531 A | | 8/1996 | Rava et al. |
| 5,556,752 A | * | 9/1996 | Lockhart et al. ............... 436/6 |
| 5,567,583 A | | 10/1996 | Wang et al. |
| 5,571,639 A | | 11/1996 | Hubbell et al. |
| 5,578,832 A | | 11/1996 | Trulson et al. |
| 5,700,637 A | | 12/1997 | Southern |
| 5,837,832 A | | 11/1998 | Chee et al. |
| 5,861,242 A | | 1/1999 | Chee et al. |
| 5,874,219 A | * | 2/1999 | Rava et al. ..................... 435/6 |
| 2002/0048754 A1 | | 4/2002 | Lockhart et al. |

FOREIGN PATENT DOCUMENTS

| | | | | |
|---|---|---|---|---|
| WO | WO 89/10977 | 11/1989 | ............ | C12Q/1/68 |
| WO | WO 90/15070 | 12/1990 | ............ | C07K/1/04 |
| WO | WO 92/10092 | 6/1992 | ............ | A01N/1/02 |
| WO | WO 95/11995 | 5/1995 | ............ | C12Q/1/68 |

OTHER PUBLICATIONS

Materials from HYSEQ Inc.: "Genome Sequencing Machine", p. 60; summary materials—5 pgs.
Drmanac,R.T., "Sequencing By Hybridization (SBH) On Super Chips" presented at "Biochip Array Technologies, Fabrication & Application", Meeting May 10, 1995, Wash. D.C.
Fodor, S.P.A. et al., "Multiplexed Biochemical Assays With Biological Chips", Nature 364:555–556 (1993).
Pease, A.C., et al., "Light–generated Oligonucleotide Arrays for Rapid DNA Sequence Analysis", Proc. Natl. Acad. Sci. USA, 91:5022–5026 (1994).
Albin, M., et al., "Sensitivity Enhancement for Capillary Electrophoresis", Analytical Chemistry, 65(10):489A–497A (1993).
Fodor, S.P.A. et al., "Light–Directed, Spatially Addressable Parallel Chemical Synthesis", Science 251:767 (1991).
Monnig, C.A. & Kennedy, R.T., "Capillary Electrophoresis", Analytical Chemistry 66(12):280R–314R (1994).
Matthews, J.A. and Kricka L.J., "Analytical Strategies for the Use of DNA Probes," Analyt. Biochem. 169:1–25 (1988).
U.S. patent application No. 07/624,120, by Fodor et al., filed Dec. 6, 1990.
U.S. patent application No. 08/082,937, by Fodor et al., filed Jun. 25, 1993.
U.S. patent application No. 08/143,312, by Chee et al., filed Oct. 26, 1993.
U.S. patent application No. 08/284,064, by Chee et al., filed Aug. 2, 1994.
Drmanac, Diochip Array Technologies Fabrication & Applications, May 10, 1995.*
Matthews et al. Analytical Biochemistry, vol. 169, pp. 1–25, 1988.*

* cited by examiner

*Primary Examiner*—Kenneth R. Horlick
*Assistant Examiner*—Cynthia Wilder
(74) *Attorney, Agent, or Firm*—Hamilton, Brook, Smith & Reynolds, P.C.

(57) ABSTRACT

Methods for concurrently processing multiple biological chip assays by providing a biological chip plate comprising a plurality of test wells, each test well having a biological chip having a molecular probe array; introducing samples into the test wells; subjecting the biological chip plate to manipulation by a fluid handling device that automatically performs steps to carry out reactions between target molecules in the samples and probes; and subjecting the biological chip plate to a biological chip plate reader that interrogates the probe arrays to detect any reactions between target molecules and probes.

31 Claims, 8 Drawing Sheets

METHODS FOR CONCURRENTLY PROCESSING MULTIPLE BIOLOGICAL CHIP ASSAYS

This application is a continuation of U.S. application Ser. No. 09/247,430, filed Feb. 10, 1999 now abandoned, which is a continuation of U.S. application Ser. No. 08/630,051, filed Apr. 9, 1996, now U.S. Pat. No. 5,874,219, which is a continuation of U.S. application Ser. No. 08/476,850, filed Jun. 7, 1995, now U.S. Pat. No. 5,545,531. The entire teachings of the above applications are incorporated herein by reference.

BACKGROUND OF THE INVENTON

This invention relates to methods for concurrently performing multiple biological chip assays. The invention therefore relates to diverse fields impacted by the nature of molecular interaction, including chemistry, biology, medicine and diagnostics.

New technology, called VLSIPS™, has enabled the production of chips smaller than a thumbnail that contain hundreds of thousands or more of different molecular probes. These biological chips or arrays have probes arranged in arrays, each probe assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

Biological chips or arrays are useful in a variety of screening techniques for obtaining information about either the probes or the target molecules. For example, a library of peptides can be used as probes to screen for drugs. The peptides can be exposed to a receptor, and those probes that bind to the receptor can be identified.

Arrays of nucleic acid probes can be used to extract sequence information from, for example, nucleic acid samples. The samples are exposed to the probes under conditions that allow hybridization. The arrays are then scanned to determine to which probes the sample molecules have hybridized. One can obtain sequence information by careful probe selection and using algorithms to compare patterns of hybridization and non-hybridization This method is useful for sequencing nucleic acids, as well as sequence checking. For example, the method is useful in diagnostic screening for genetic diseases or for the presence and/or identity of a particular pathogen or a strain of pathogen. For example, there are various strains of HIV, the virus that causes AIDS. Some of them have become resistant to current AIDS therapies. Diagnosticians can use DNA arrays to examine a nucleic acid sample from the virus to determine what strain it belongs to.

Currently, chips are treated individually, from the step of exposure to the target-molecules to scanning. These methods yield exquisitely detailed information. However, they are not adapted for handling multiple samples simultaneously. The ability to do so would be advantageous in settings in which large amounts of information are required quickly, such as in clinical diagnostic laboratories or in large-scale undertakings such as the Human Genome Project.

SUMMARY OF THE INVENTION

This invention provides methods for concurrently processing multiple biological chip assays. According to the methods, a biological chip plate comprising a plurality of test wells is provided. Each test well defines a space for the introduction of a sample and contains a biological array. The array is formed on a surface of the substrate, with the probes exposed to the space. A fluid handling device manipulates the plates to perform steps to carry out reactions between the target molecules in samples and the probes in a plurality of test wells. The biological chip plate is then interrogated by a biological chip plate reader to detect any reactions between target molecules and probes in a plurality of the test wells, thereby generating results of the assay. In a further embodiment of the invention, the method also includes processing the results of the assay with a computer. Such analysis is useful when sequencing a gene by a method that uses an algorithm to process the results of many hybridization assays to provide the nucleotide sequence of the gene.

The methods of the invention can involve the binding of tagged target molecules to the probes. The tags can be, for example, fluorescent markers, chemiluminescent markers, light scattering markers or radioactive markers. In certain embodiments, the probes are nucleic acids, such as DNA or RNA molecules. The methods can be used to detect or identify a pathogenic organism, such as HIV, or to detect a human gene variant, such a the gene for a genetic disease such as cystic fibrosis, diabetes, muscular dystrophy or predisposition to certain cancers.

This invention also provides systems for performing the methods of this invention. The systems include a biological chip plate; a fluid handling device that automatically performs steps to carry out assays on samples introduced into a plurality of the test wells; a biological chip plate reader that determines in a plurality of the test wells the results of the assay and, optionally, a computer comprising a program for processing the results. The fluid handling device and plate reader can have a heater/cooler controlled by afthermostat for controlling the temperature of the samples in the test wells and robotically controlled pipets for adding or removing fluids from the test wells at predetermined times.

In certain embodiments, the probes are attached by light-directed probe synthesis. The biological chip plates can have 96 wells arranged in a rows and 12 columns, such as a standard microtiter plate. The probe arrays can each have at least about 100, 1000, 100,000 or 1,000,000 addressable features (e.g., probes). A variety of probes can be used on the plates, including, for example, various polymers such as peptides or nucleic acids.

The plates can have wells in which the probe array in each test well is the same. Alternatively, when each of several samples are to be subjected to several tests, each row can have the same probe array and each column can have a different array. Alternatively, all the wells can have different arrays.

Several methods of making biological chip plates are contemplated. In one method, a wafer and a body are provided. The wafer includes a substrate and a surface to which is attached a plurality of arrays of probes. The body has a plurality of channels. The body is attached to the surface of the wafer whereby the channels each cover an array of probes and the wafer closes one end of a plurality of the channels, thereby forming test wells defining spaces for receiving samples. In a second method, a body having a plurality of wells defining spaces is provided and biological chips are provided. The chips are attached to the wells so that the probe arrays are exposed to the space. Another embodiment involves providing a wafer having a plurality of probe arrays; and applying a material resistant to the flow of a liquid sample so as to surround the probe arrays, thereby creating test wells.

This invention also provides a wafer for making a biological chip plate. The wafer has a substrate and a surface to which are attached a plurality of probe arrays. The probe arrays are arranged on the wafer surface in rows and columns, wherein the probe arrays in each row are the same and the probe arrays in each column are different.

DETAILED DESCRIPTION OF THE INVENTION

I. Definitions

Figure 1:
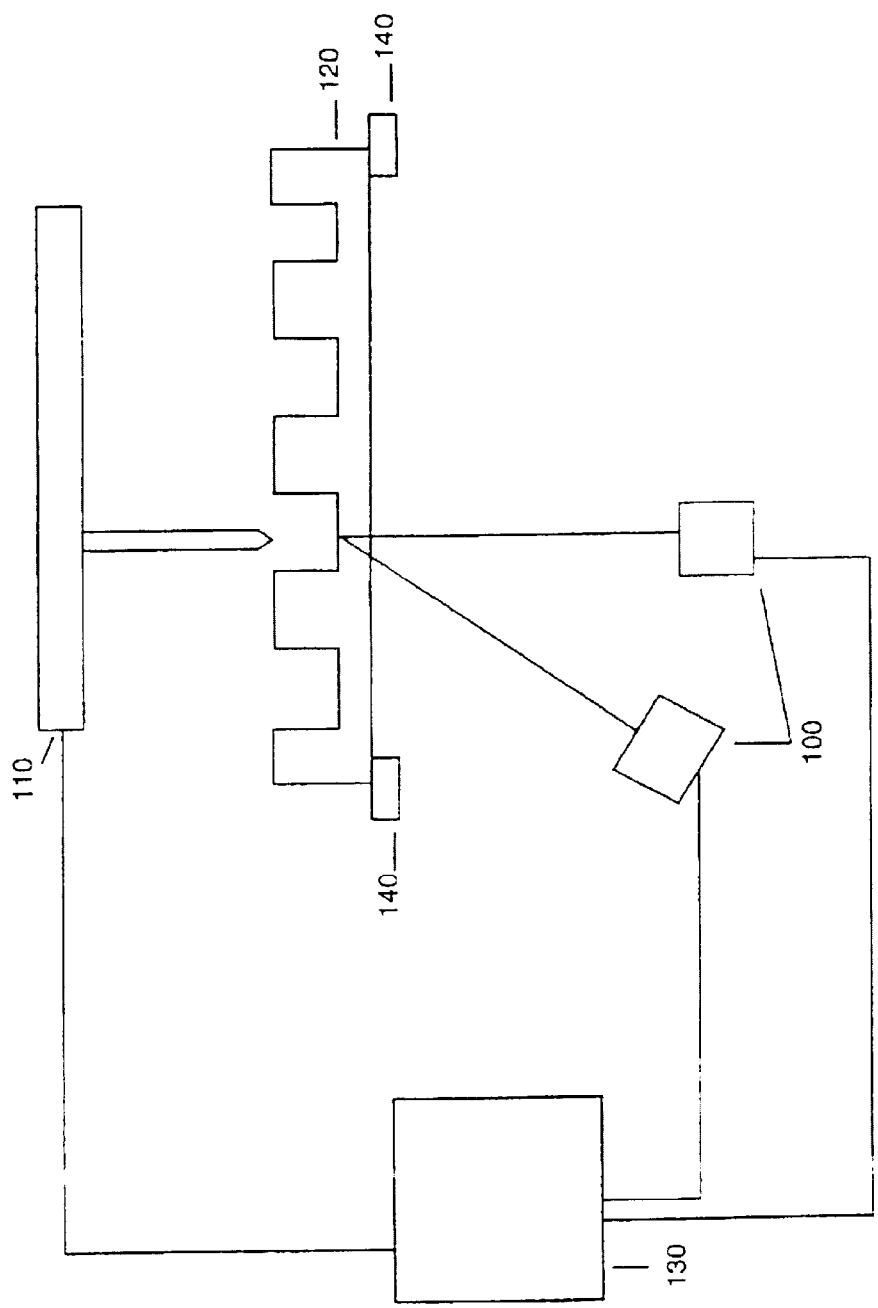
FIG. 1 depicts a system of this invention having a biological chip plate, fluid handling device, biological chip plate reader and computer.

The following terms are intended to have the following general meanings as they are used herein:

A. Complementary: Refers to the topological compatibility or matching together of interacting surfaces of a probe molecule and its target. Thus, the target and its probe can be described as complementary, and furthermore, the contact surface characteristics are complementary to each other.

B. Probe: A probe is a surface-immobilized molecule that can be recognized by a particular target. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

C. Taraet: A molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

D. Array: A collection of probes, at least two of which are different, arranged in a spacially defined and physically addressable manner.

E. Biological chip: A substrate having a surface to which one or more arrays of probes is attached. The substrate can be, merely by way of example, silicon or glass and can have the thickness of a glass microscope slide or a glass cover slip. Substrates that are transparent to light are useful when the method of performing an assay on the chip involves optical detection. As used herein, the term also refers to a probe array and the substrate to which it is attached that form part of a wafer.

F. Wafer: A substrate having a surface to which a plurality of probe arrays are attached. On a wafer, the arrays are physically separated by a distance of at least about a millimeter, so that individual chips can be made by dicing a wafer or otherwise physically separating the array into units having a probe array.

G. Bioloaical ChiR Plate: A device having an array of biological chips in which the probe array of each chip is separated from the probe array of other chips by a physical barrier resistant to the passage of liquids and forming an area or space, referred to as a "test well," capable of containing liquids in contact with the probe array.

II. General

This invention provides automated methods for concurrently processing multiple biological chip assays. Currently available methods utilize each biological chip assay individually. The methods of this invention allow many tests to be set up and processed together. Because they allow much higher throughput of test samples, these methods greatly improve the efficiency of performing assays on biological chips.

In the methods of this invention, a biological chip plate is provided having a plurality of test wells. Each test well includes a biological chip. Test samples, which may contain target molecules, are introduced into the test wells. A fluid handling device exposes the test wells to a chosen set of reaction conditions by, for example, adding or removing fluid from the wells, maintaining the liquid in the wells at predetermined temperatures, and agitating the wells as required, thereby performing the, test. Then, a biological chip reader interrogates the probe arrays in the test wells, thereby obtaining the results of the tests. A computer having an appropriate program can further analyze the results from the tests.

Referring to FIG. 1, one embodiment of the invention is a system for concurrently processing biological chip assays. The system includes a biological chip plate reader 100, a fluid handling device 110, a biological chip plate 120 and, optionally, a computer 130. In operation, samples are placed in wells on the chip plate 120 with fluid handling device 110. The plate optionally can be moved with a stage translation device 140. Reader 100 is used to identify where targets in the wells have bound to complementary probes. The system operates under control of computer 130 which may optionally interpret the results of the assay.

A. Biological Chip Plate Reader

In assays performed on biological chips, detectably labeled target molecules bind to probe molecules. Reading the results of an assay involves detecting a signal produced by the detectable label. Reading assays on a biological chip plate requires a.biological chip reader. Accordingly, locations at which target(s) bind with complementary probes can be identified by detecting the location of the label. Through knowledge of the characteristics/sequence of the probe versus location, characteristics of the target can be determined. The nature of the biological chip reader depends upon the particular type of label attached to the target molecules.

The interaction between targets and probes can be characterized in terms of kinetics and thermodynamics. As such, it may be necessary to interrogate the array while in contact with a solution of labeled targets. In such systems, the detection system must be extremely selective, with the capacity to discriminate between surface-bound and solution-born targets. Also, in order to perforn a quantitative analysis, the high-density of the probe sequences requires the system to have the capacity to distinguish between each feature site, The system also should have sensitivity to low signal and a large dynamic range.

In one embodiment, the chip plate reader includes a confocal detection device having a monochromatic or polychromatic light source, a focusing system for directing an excitation light from the light source to the substrate, a temperature controller for controlling the substrate temperature during a reaction, and a detector for detecting fluorescence emitted by the targets in response to the excitation light. The detector for detecting the fluorescent emissions from the substrate, in some embodiments, includes a photomultiplier tube. The location to which light is directed may be controlled by, for example, an x-y-z translation table. Translation of the x-y-z table, temperature control, and data collection are managed and recorded by an appropriately programmed digital computer.

Further details for methods of detecting fluorescently labelled materials on biological chips are provided in U.S. patent application Ser. No. 08/195,889, filed Feb. 10, 1994 and incorporated herein by reference.

Figure 2:
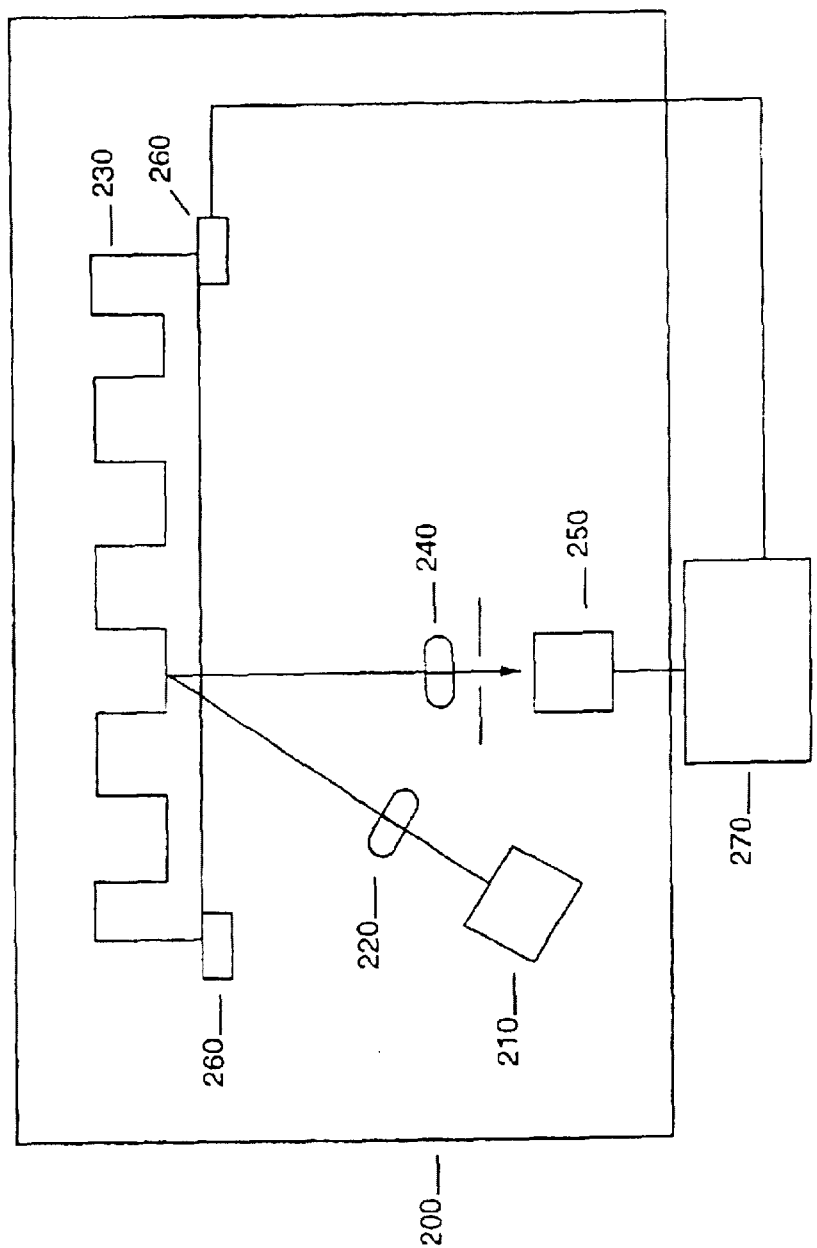
FIG. 2 depicts the scanning of a biological chip plate by a biological chip plate reader.

FIG. 2 illustrates the reader according to one specific embodiment. The chip plate reader comprises a body 200 for immobilizing the biological chip plate. Excitation radiation, from an excitation source 210 having a first wavelength, passes through excitation optics 220 from below the array. The light passes through the chip plate since it is transparent to at least this wavelength of light. The excitation radiation excites a region of a probe array on the biological chip plate 230. In response, labeled material on the sample emits radiation which has a wavelength that is different from the excitation wavelength. Collection optics 240, also below the array, then collect the emission from the sample and image it onto a detector 250, which can house a CCD array, as described below. The detector generates a signal proportional to the amount of radiation sensed thereon. The signals can be assembled to represent an image associated with the plurality of regions from which the emission originated.

According to one embodiment, a multi-axis translation stage 260 moves the biological chip plate to position different wells to be scanned, and to allow different probe portions of a probe array to be interrogated. As a result, a 2-dimensional image of the probe arrays in each well is obtained.

The biological chip reader can include auto-focusing feature to maintain the sample in the focal plane of the excitation light throughout the scanning process. Further, a temperature controller may be employed to maintain the sample at a specific temperature while it is being scanned. The multi-axis translation stage, temperature controller, auto-focusing feature, and electronics associated with imaging and data collection are managed by an appropriately programmed digital computer 270.

In one embodiment, a beam is focused onto a spot of about 2 $\mu$m in diameter on the surface of the plate using, for example, the objective lens of a microscope or other optical means to control beam diameter. (See, e.g., U.S. patent application Ser. No. 08/195,889, supra.)

In another embodiment, fluorescent probes are employed in combination with CCD imaging systems. Details of this method are described in U.S. application Ser. No. 08/301,051, incorporated herein by reference in its entirely. In many commercially available microplate readers, typically the light source is placed above a well, and a photodiode detector is below the well. In the present invention, the light source can be replaced with a higher power lamp or laser. In one embodiment, the standard absorption geometry is used, but the photodiode detector is replaced with a CCD camera and imaging optics to allow rapid imaging of the well. A series of Raman holographic or notch filters can be used in the optical path to eliminate the excitation light while allowing the emission to pass to the detector. In a variation of this method, a fiber optic imaging bundle is utilized to bring the light to the CCD detector. In another embodiment, the laser is placed below the biological chip plate and light directed through the transparent wafer or base that forms the bottom of the biological chip plate. In another embodiment, the CCD array is built into the wafer of the biological chip plate.

The choice of the CCD array will depend on the number of probes in each biological array. If 2500 probes nominally arranged in a square (50×50) are examined, and 6 lines in each feature are sampled to obtain a good image, then a CCD array of 300×300 pixels is desirable in this area. However, if an individual well has 48,400 probes (220×220) then a CCD array with 1320×1320 pixels is desirable. CCD detectors are commercially available from, e.g., Princeton Instruments, which can meet either of these requirements.

In another embodiment, the detection device comprises a line scanner, as described in U.S. patent application Ser. No. 08/301,051, filed Sep. 2, 1994, incorporated herein by reference. Excitation optics focuses excitation light to a line at a sample, simultaneously scanning or imaging a strip of the sample. Surface bound labeled targets from the sample fluoresce in response to the light. Collection optics image the emission onto a linear array of light detectors. By employing confocal techniques, substantially only emission from the light's focal plane is imaged. Once a strip has been scanned, the data representing the 1-dimensional image are stored in the memory of a computer. According to one embodiment, a multi-axis translation stage moves the device at a constant velocity to continuously integrate and process data. Alternatively, galvometric scanners or rotating polyhedral mirrors may be employed to scan the excitation light across the sample. As a result, a 2-dimensional image of the sample is obtained.

In another embodiment, collection optics direct the emission to a spectrograph which images an emission spectrum onto a 2-dimensional array of light detectors. By using a spectrograph, a full spectrally resolved image of the sample is obtained.

The read time for a full microtiter plate will depend on the photophysics of the fluorophore (i.e. fluorescence quantum yield and photodestruction yield) as well as the sensitivity of the detector. For fluorescein, sufficient signal-to-noise to read a chip image with a CCD detector can be obtained in about 30 seconds using 3 mW/cm$^2$ and 488 nm excitation from an Ar ion laser or lamp. By increasing the laser power, and switching to dyes such as CY3 or CY5 which have lower photodestruction yields and whose emission more closely matches the sensitivity maximum of the CCD detector, one easily is able to read each well in less than 5 seconds. Thus, an entire plate could be examined quantitatively in less than 10 minutes, even if the whole plate has over 4.5 million probes.

A computer can transform the data into another format for presentation. Data analysis can include the steps of determining, e.g., fluorescent intensity as a function of substrate position from the data collected, removing "outliers" (data deviating from a predetermined statistical distribution), and calculating the relative binding affinity of the targets from the remaining data. The resulting data can be displayed as an image with color in each region varying according to the light emission or binding affinity between targets and probes therein.

One application of this system when coupled with the CCD imaging system that speeds performance of the tests is to obtain results of the assay by examining the on- or off-rates of the hybridization. In one embodiment of this method, the amount of binding at each address is determined at several time points after the probes are contacted with the sample. The amount of total hybridization can be determined as a function of the kinetics of binding based on the amount of binding at each time point. Thus, it is not necessary to wait for equilibrium to be reached. The dependence of the hybridization rate for different oligonucleotides on temperature, sample agitation, washing conditions (e.g. pH, solvent characteristics, temperature) can easily be determined in order to maximize the conditions for rate and signal-to-noise. Alternative methods are described in Fodor et al., U.S. Pat. No. 5,324,633, incorporated herein by reference.

B. Fluid Handling Instruments and Assay Automation

Assays on biological arrays generally include contacting a probe array with a sample under the selected reaction conditions, optionally washing the well to remove unreacted molecules, and analyzing the biological array for evidence of reaction between target molecules the probes. These steps involve handling fluids. The methods of this invention automate these steps so as to allow multiple assays to be performed concurrently. Accordingly, this invention employs automated fluid handling systems for concurrently performing the assay steps in each of the test wells. Fluid handling allows uniform treatment of samples in the wells. Microtiter robotic and fluid-handling devices are available commercially, for example, from Tecan AG.

The plate is introduced into a holder in the fluid-handling device. This robotic device is programmed to set appropriate reaction conditions, such as temperature, add samples to the test wells, incubate the test samples for an appropriate time, remove unreacted samples, wash the wells, add substrates as appropriate and perform detection assays. The particulars of the reaction conditions depends upon the purpose of the assay. For example, in a sequencing assay involving DNA hybridization, standard hybridization conditions are chosen. However, the assay may involve testing whether a sample contains target molecules that react to a probe under a specified set of reaction conditions. In this case, the reaction conditions are chosen accordingly.

C. Biological Chip Plates

Figure 3:
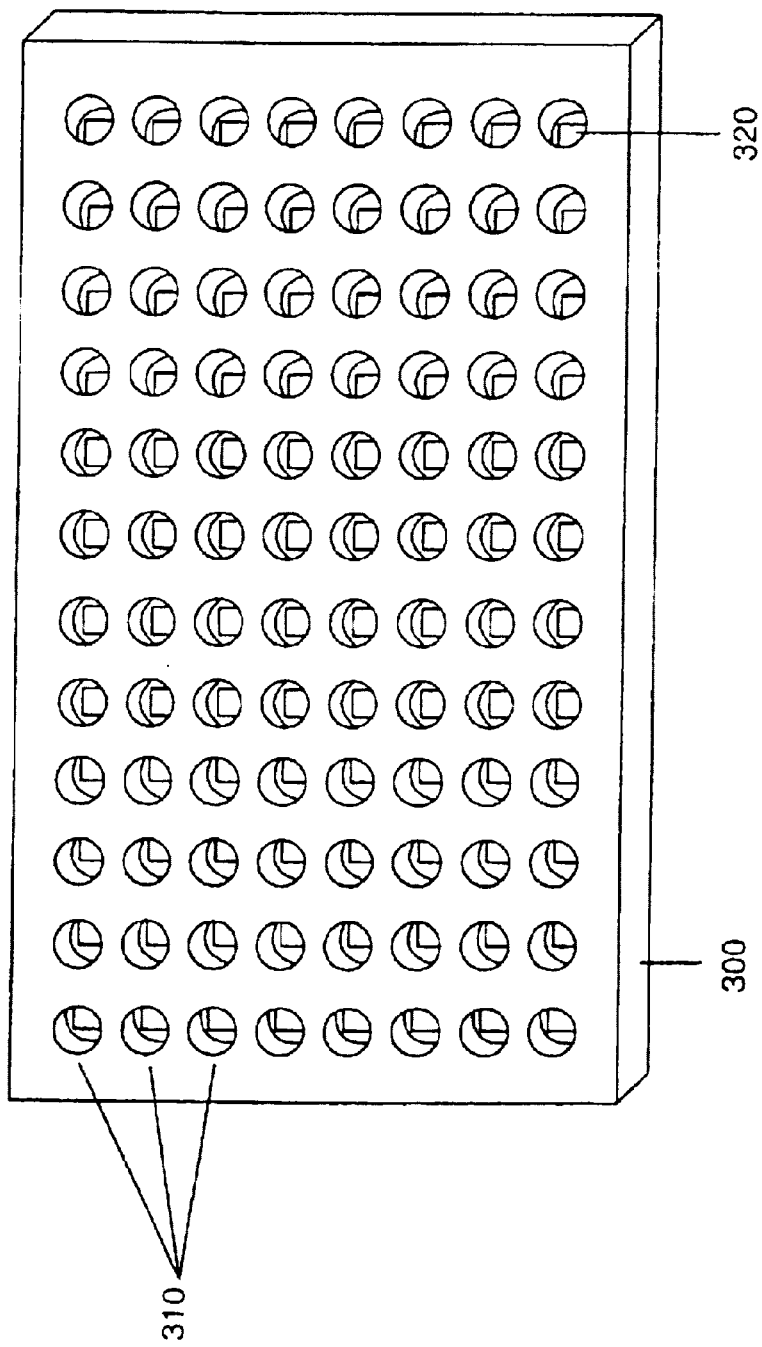
FIG. 3 depicts a biological plate of this invention.
Figure 7:
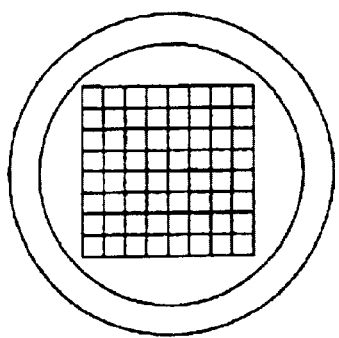
FIG. 7 is a top-down view of a test well containing a biological array.

FIG. 3 depicts an example of a biological chip plate 300 used in the methods of this invention based on the standard 96-well microtiter plate in which the chips are located at the bottom of the wells. Biological chip plates include a plurality of test wells 310, each test well defining an area or space for the introduction of a sample, and each test well comprising a biological chip 320, i.e., a substrate and a surface to which an array of probes is attached, the probes being exposed to the space. FIG. 7 shows a top-down view of a well of a biological chip plate of this invention containing a biological chip on the bottom surface of the well.

Figure 4:
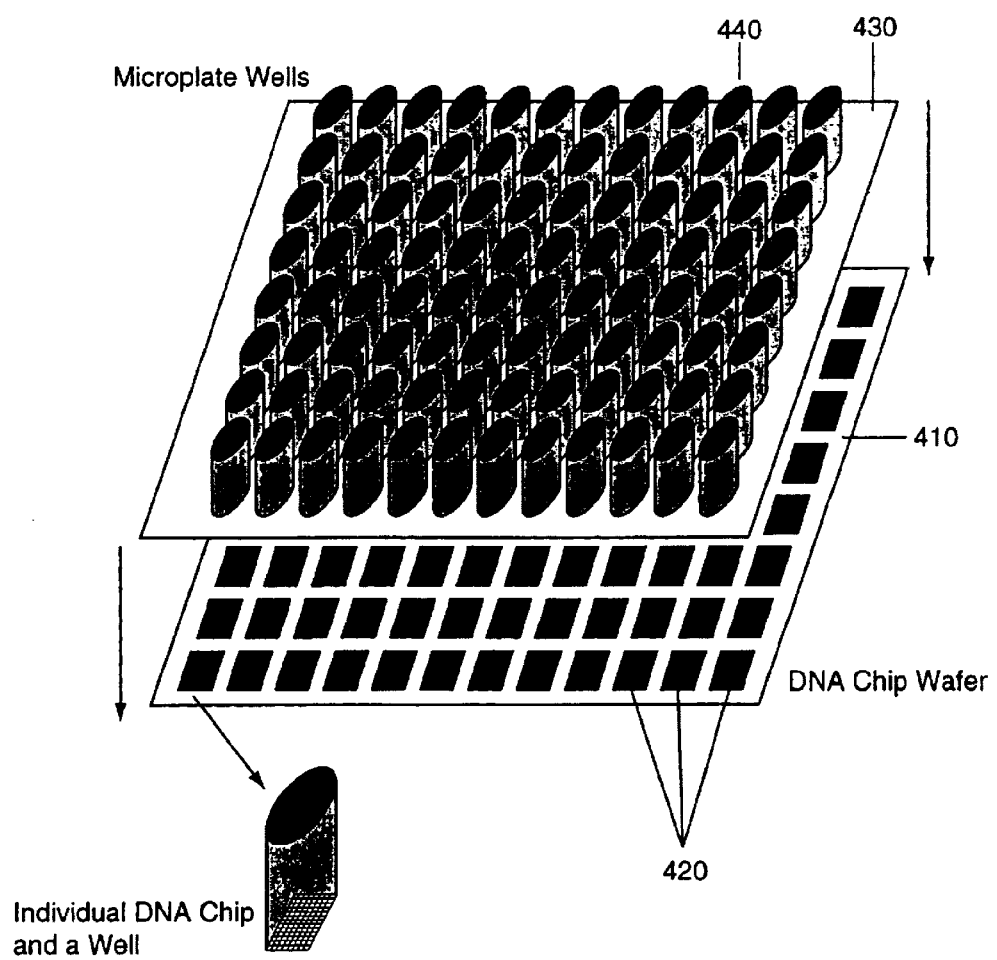
FIG. 4 depicts the mating of a wafer containing many biological arrays with a body having channels to create a biological chip plate.
Figure 5:
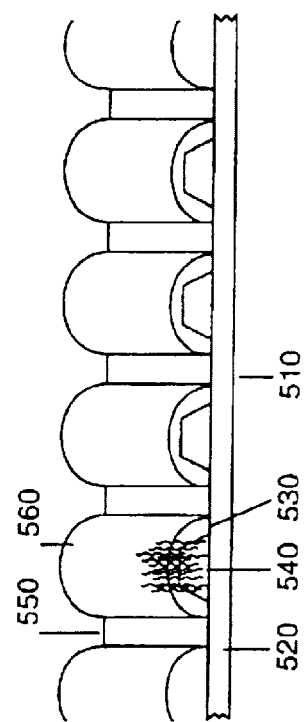
FIG. 5 depicts a biological chip plate in cross section having a body attached to a wafer to create closed test wells in which a probe array is exposed to the space in the test well.

This invention contemplates a number of embodiments of the biological chip plate. In a preferred embodiment, depicted in FIG. 4, the biological chip plate includes two parts. One part is a wafer 410 that includes a plurality of biological arrays 420. The other part is the body of the plate 430 that contains channels 440 that form the walls of the well, but that are open at the bottom. The body is attached to the surface of the wafer so as to close one end of the channels, thereby creating wells. The walls of the channels are placed on the wafer so that each surrounds and encloses the probe array of a biological array. FIG. 5 depicts a cross-section of this embodiment, showing the wafer 510 having a substrate 520 (preferably transparent to light) and a surface 530 to which is attached an array of probes 540. A channel wall 550 covers a probe array on the wafer, thereby creating well spaces 560. The wafer can be attached to the body by any attachment means known in the art, for example, gluing (e.g., by ultraviolet-curing epoxy or various sticking tapes), acoustic welding, sealing such as vacuum or suction sealing, or even by relying on the weight of the body on the wafer to resist the flow of fluids between test wells.

Figure 6:
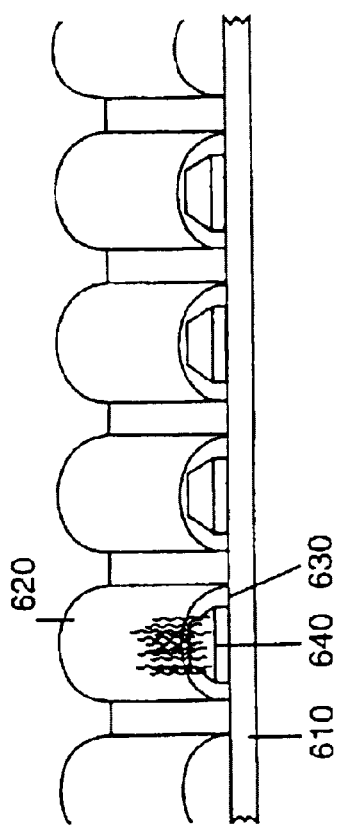
FIG. 6 depicts a biological plate in cross section having a body which has individual biological chips attached to the bottom of the wells.

In another preferred embodiment, depicted in cross section in FIG. 6, the plates include a body 610 having pre-formed wells 620, usually flat-bottomed. Individual biological chips 630 are attached to the bottom of the wells so that the surface containing the array of probes 640 is exposed to the well space where the sample is to be placed.

In another embodiment, the biological chip plate has a wafer having a plurality of probe arrays and a material resistant to the flow of a liquid sample that surrounds each probe array. For example, in an embodiment useful for testing aqueous-based samples, the wafer can be scored with waxes, tapes or other hydrophobic materials in the spaces between the arrays, forming cells that act as test wells. The cells thus contain liquid applied to an array by resisting spillage over the barrier and into another cell. If the sample contains a non-aqueous solvent, such as an alcohol, the material is selected to be resistant to corrosion by the solvent.

The microplates of this invention have a plurality of test wells that can be arrayed in a variety of ways. In one embodiment, the plates have the general size and shape of standard-sized microtiter plates having 96 wells arranged in an 8×12 format. One advantage of this format is that instrumentation already exists for handling and reading assays on microtiter plates. Therefore, using such plates in biological chip assays does not involve extensive re-engineering of commercially available fluid handling devices. However, the plates can have other formats as well.

The material from which the body of the biological chip plate is made depends upon the use to which it is to be put. In particular, this invention contemplates a variety of polymers already used for microtiter plates including, for example, (poly)tetrafluoroethylene, (poly)vinylidenedifluoride, polypropylene, polystyrene, polycarbonate, or combinations thereof. When the assay is to be performed by sending an excitation beam through the bottom of the plate collecting data through the bottom of the plate, the body of the plate and the substrate of the chip should be transparent to the wavelengths of light being used.

The arrangement of probe arrays in the wells of a microplate depends on the particular application contemplated. For example, for diagnostic uses involving performing the same test on many samples, every well can have the same array of probes. If several different tests are to be performed on each sample, each row of the plate can have the same array of probes and each column can contain a different array. Samples from a single patient are introduced into the wells of a particular column. Samples from a different patient are introduced into the wells of a different column. In still another embodiment, multiple patient samples are introduced into a single well. If a well indicates a "positive" result for a particular characteristic, the samples from each patient are then rerun, each in a different well, to determine which patient sample gave a positive result.

D. Biological Chips

The biological chip plates used in the methods of this invention include biological chips. The array of probe sequences can be fabricated on the biological chip according to the pioneering techniques disclosed in U.S. Pat. No. 5,143,854, PCT WO 92/10092, PCT WO 90/15070, or U.S. application Ser. Nos. 08/249,188, 07/624,120, and 08/082,937, incorporated herein by reference for all purposes. The combination of photolithographic and fabrication techniques may, for example, enable each probe sequence ("feature") to occupy a very small area ("site" or "location") on the support. In some embodiments, this feature site may be as small as a few microns or even a single molecule. For example, a probe array of 0.25 mm$^2$ (about the size that would fit in a well of a typical 96-well microtiter plate) could have at least 10, 100, 1000, $10^4$, $10^5$ or $10^6$ features. In an alternative embodiment, such synthesis is performed according to the mechanical techniques disclosed in U.S. Pat. No. 5,384,261, incorporated herein by reference.

Figure 8:
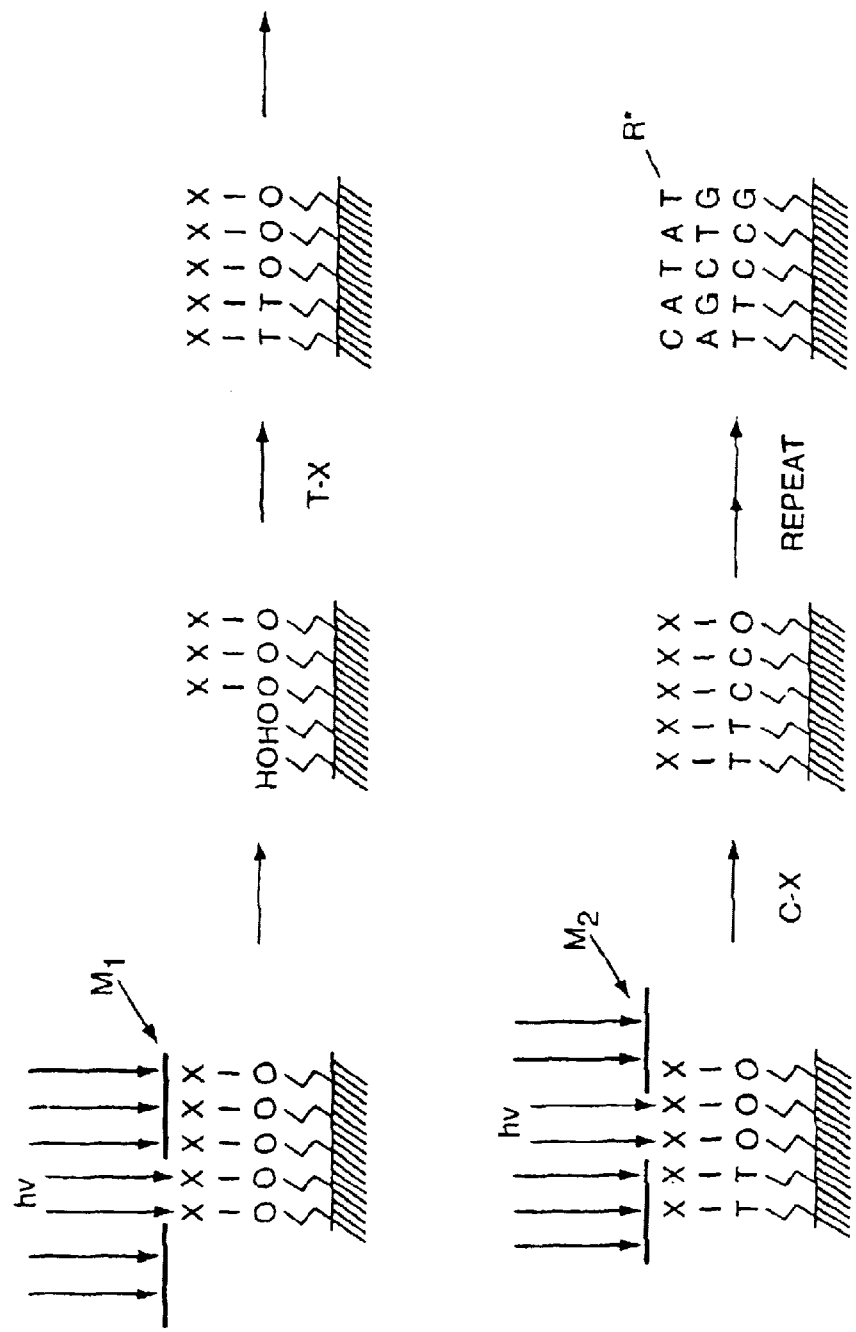
FIG. 8 depicts a method of producing an array of oligonucleotide probes on the surface of a substrate by using a mask to expose certain parts of the surface to light, thereby removing photoremovable protective groups, and attaching nucleotides to the exposed reactive groups.

Referring to FIG. 8, in general, linker molecules, $^-$O-X, are provided on a substrate. The substrate is preferably flat but may take on a variety of alternative surface configurations. For example, the substrate may contain raised or depressed regions on which the probes are located. The substrate and its surface preferably form a rigid support on which the sample can be formed. The substrate and its surface are also chosen to provide appropriate light-absorbing characteristics. For instance, the substrate may be functionalized glass, Si, Ge, Gabs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polypropylene, or combinations thereof. Other substrate materials will be readily apparent to those of skill in the art upon review of this disclosure. In a preferred embodiment the substrate is flat glass or silica.

Surfaces on the solid substrate usually, though not always, are composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically.transparent and will have surface Si—OH functionalities, such as those found on silica surfaces.

A terminal end of the linker molecules is provided with a.reactive functional group protected with a photoremovable protective group, 0-X. Using lithographic methods, the photoremovable protective group is exposed to light, hv, through a mask, $M_1$, that exposes a selected portion of the surface, and removed from the linker molecules in first selected regions. The substrate is then washed or otherwise contacted with a first monomer that reacts with exposed functional groups on the linker molecules ($^-$T-X). In the case of nucleic acids, the monomer can be a phosphoramidite activated nucleoside protected at the 5'-hydroxyl with a photolabile protecting group.

A second set of selected regions, thereafter, exposed to light through a mask, $M_2$, and photoremovable protective group on the linker molecule/protected amino acid or nucleotide is removed at the second set of regions. The substrate is then contacted with a second monomer containing a photoremovable protective group for reaction with exposed functional groups. This process is repeated to selectively apply monomers until polymers of a desired length and desired chemical sequence are obtained. Photolabile groups are then optionally removed and the sequence is, thereafter, optionally capped. Side chain protective groups, if present, are also removed.

The general process of synthesizing probes by removing protective groups by exposure to light, coupling monomer units to the exposed active sites, and capping unreacted sites is referred to herein as "light-directed probe synthesis." If the probe is an oligonucleotide, the process is referred to as "light-directed oligonucleotide synthesis" and so forth.

The probes can be made of any molecules whose synthesis irvolves sequential addition of units. This includes polymers composed of a series of attached units and molecules bearing a common skeleton to which various functional groups are added. Polymers useful as probes in this invention include, for example, both linear and cyclic polymers of nucleic acids, polysaccharides, phospholipids, and peptides having either $\alpha$-, $\beta$-, or $\omega$-amino acids, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure. Molecules bearing a common skeleton include benzodiazepines and other small molecules, such as described in U.S. Pat. No. 5,288,514, incotdorated herein by reference.

Preferably, probes are arrayed on a chip in addressable rows and columns in which the dimensions of the chip conform to the dimension of the plate test well. Technologies already have been developed to read information from such arrays. The amount of information that can be stored on each plate of chips depends on the lithographic density which is used to synthesize the wafer. For example, if each feature size is about 100 microns on a side, each array can have about 10,000 probe addresses in a 1 cm$^2$ area. A plate having 96 wells would contain about 192,000 probes. However, if the arrays have a feature size of 20 microns on a side, each array can have close to 50,000 probes and the plate would have over 4,800,000 probes.

The selection of probes and their organization in an array depends upon the use to which the biological chip will be put. In one embodiment, the chips are used to sequence or re-sequence nucleic acid molecules, or compare their sequence to a referent molecule. Re-sequencing nucleic acid molecules involves determining whether a particular molecule has any deviations from the sequence of reference molecule. For example, in one embodiment, the plates are used to identify in a particular type of HIV in a set of patient samples. Tiling strategies for sequence checking of nucleic acids are described in U.S. patent application Ser. No. 08/284,064 (PCT/US94/12305), incorporated herein by reference.

In typical diagnostic applications, a solution containing one or more targets to be identified (i.e., samples from patients) contacts the probe array. The targets will bind or hybridize with complementary probe sequences. Accordingly, the probes will be selected to have sequences directed to (i.e., having at least some complementarity with) the target sequences to be detected, e.g., human or pathogen sequences. Generally, the targets are tagged with a detectable label. The detectable label can be, for example, a luminescent label, a light scattering label or a radioactive label. Accordingly, locations at which targets hybridize with complimentary probes can be identified by locating the markers. Based on the locations where hybridization occurs, information regarding the target sequences can be extracted. The existence of a mutation may be determined by comparing the target sequence with the wild type.

In a preferred embodiment, the detectable label is a luminescent label. Useful luminescent labels include fluorescent labels, chemi-luminescent labels, bio-luminescent labels, and calorimetric labels, among others. Most preferably, the label is a fluorescent label such as fluorescein, rhodamine, cyanine and so forth. Fluorescent labels include, inter alia, the commercially available fluorescein phosphoramidites such as Fluoreprime (Pharmacia), Fluoredite (Millipore) and FAM (ABI). For example, the entire surface of the substrate is exposed to the activated fluorescent phosphoramidite, which reacts with all of the deprotected 5'-hydroxyl groups. Then the entire substrate is exposed to an alkaline solution (eg., 50% ethylenediamine in ethanol for 1–2 hours at room temperature). This is necessary to remove the protecting groups from the fluorescein tag.

To avoid self-quenching interactions between fluorophores on the surface of a biological chip, the fluorescent tag monomer should be diluted with a non-fluorescent analog of equivalent reactivity. For example, in the case of the fluorescein phosphoramidites noted above, a 1:20 dilution of the reagent with a non-fluorescent phosphoramidite such as the standard 5'-DMT-nucleoside phosphoramidites, has been found to be suitable. Correction for background non-specific binding of the fluorescent reagent and other such effects can be determined by routine testing.

Useful light scattering labels include large colloids, and especially the metal colloids such as those from gold, selenium and titanium oxide.

Radioactive labels include, for example, $^{32}P$. This label can be detected by a phosphoimager. Detection of course, depends on the resolution of the imager. Phosophoimagers are available having resolution of 50 microns. Accordingly, this label is currently useful with chips having features of that size.

E. Uses

The methods of this invention will find particular use wherever high through-out of samples is required. In particular, this invention is useful in clinical settings and for sequencing large quantities of DNA, for example in connection with the Human Genome project.

The clinical setting requires performing the same test on many patient samples. The automated methods of this invention lend themselves to these uses when the test is one appropriately performed on a biological chip. For example, a DNA array can determine the particular strain of a pathogenic organism based on characteristic DNA sequences of the strain. The advanced techniques based on these assays now can be introduced into the clinic. Fluid samples from several patients are introduced into the test wells of a biological chip plate and the assays are performed concurrently.

In some embodiments, it may be desirable to perform multiple tests on multiple patient samples concurrently. According to such embodiments, rows (or columns) of the microtiter plate will contain probe arrays for diagnosis of a particular disease or trait. For example, one row might contain probe arrays designed for a particular cancer, while other rows contain probe arrays for another cancer. Patient samples are then introduced into respective columns (or rows) of the microtiter plate. For example, one column may be used to introduce samples from patient "one," another column for patient "two" etc. Accordingly, multiple diagnostic tests may be performed on multiple patients in parallel. In still further embodiments, multiple patient samples are introduced into a single well. in a particular well indicator the presence of a genetic disease or other characteristic, each patient sample is then individually processed to identify which patient exhibits that disease or trait. For relatively rarely occurring characteristics, further order-of-magnitude efficiency may be obtained according to this embodiment.

Particular assays that will find use in automation include those designed specifically to detect or identify particular variants of a pathogenic organism, such as HIV. Assays to detect or identify a human or animal gene are also contemplated. In one embodiment, the assay is the detection of a human gene variant that indicates existence of or predisposition to a genetic disease, either from acquired or inherited mutations in an individual DNA. These include genetic diseases such as cystic fibrosis, diabetes, and muscular dystrophy, as well as diseases such as cancer (the P53 gene is relevant to some cancers), as disclosed in U.S. patent application Ser. No. 08/143,312, already incorporated by reference.

The present invention provides a substantially novel method for performing assays on biological arrays. While specific examples have been provided, the above description is illustrative and not restrictive. Many variations of the invention will become apparent to those of skill in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A method for concurrently processing multiple biological chip assays comprising the steps of:
    (a) providing a biological chip plate comprising a plurality of probe arrays and, surrounding the probe arrays, material resistant to the flow of liquid, thereby forming a plurality of test wells, each test well defining a space for the introduction of a sample;
    (b) introducing into each test well test samples from a plurality ofdifferent patients, wherein each test sample contains target molecules;
    (c) manipulating the biological chip plate with a fluid handling device that automatically performs steps to carry out reactions between target molecules in the test samples and probes in a plurality of the test wells, wherein the fluid handling device controls temperature, sample handling, substrate handling and washing of the test wells; and (d) interrogating the probe arrays of the biological chip plate with a biological chip plate reader to detect reactions between target molecules and probes in a plurality of the test wells to generate assay results.

2. The method of claim 1 further comprising the step of processing the results with a computer.

3. The method of claim 2 wherein the results are processed into an image with the intensity in each region of the image varying according to the binding affinity between targets and probes.

4. The method of claim 1 wherein the probes are DNA or RNA molecules.

5. The method of claim 4 wherein
   (a) the reactions are hybridization of target molecules to probes; and
   (b) the results provide information regarding the nucleotide sequence of the target molecule.

6. The method of claim 5 wherein the assay is the detection or identification of a pathogenic organism.

7. The method of claim 6 wherein the pathogenic organism is HIV.

8. The method of claim 5 wherein the assay is the detection or identification of a human nucleic acid.

9. The method of claim 8 wherein the assay is the detection of a human gene variant.

10. The method of claim 9 wherein the human gene variant indicates the existence of, or predisposition to, cystic fibrosis, diabetes, muscular dystrophy or cancer.

11. The method of claim 1 further comprising controlling the temperature of the samples in the test wells and adding or removing fluids from the test wells at predetermined times.

12. The method, of claim 1 wherein the target molecule is tagged with a fluorescent marker, a chemiluminescent marker, a light scattering marker or a radioactive marker.

13. The method of claim 12 wherein the marker is a fluorescent marker selected from the group consisting of fluorescein, rhodamine, or cyanine.

14. The method of claim 12 wherein the biological chip plate reader comprises:
   (a) a confocal detection device having a monochromatic or polychroniatic light source;
   (b) optics for directing ail excitation light from the light source at the substrate;
   (c) a temperature controller for conrolling temperature of the substrate during a reaction; and
   (d) a detector for detecting fluorescence emitted by the targets in response to the excitation light.

15. The method of claim 1 wherein the manipulating step comprises robotically controlling pipets for adding or removing fluids from the test wells at predetermined times.

16. The method of claim 14 wherein the detector comprises a photomultiplier tube.

17. The method of claim 14 wherein the interrogating step comprises focusing the excitation light to a point on the plate and determining the region from which the fluorescence originated.

18. The method of claim 14 wherein the target is tagged with a fluorescent marker and the biological chip plate reader comprises a CCD array.

19. The method of claim 1 wherein the probe arrays each have at least about 2500 features.

20. The method of claim 1 wherein the probe arrays each have at least about 50,000 features.

21. The method of claim 1 wherein said chip plate is made by the steps of mating a wafer comprising a plurality of probe arrays to an array of open ended wells.

22. A method for concurrently processing multiple biological chip assays, comprising the steps of:
   (a) providing a biological chip plate comprising a plurality of probe arrays and, surrounding the probe arrays, material resistant to the flow of liquid, thereby forming a plurality of test wells, each test well defining a space for the introduction of a sample;
   (b) introducing into each test well test samples from a plurality of different patients, wherein each test sample contains target molecules;
   (c) manipulating the biological chip plate with a fluid handling device that automatically performs steps to carry out reactions between target molecules in the test samples and probes in a plurality of the test wells, wherein the fluid handling device controls temperature, sample handling, substrate handling and washing of the test walls; and
   (d) interrogating the probe arrays of the biological chip plate with a biological chip plate reader to detect reactions between target molecules and probes in a plurality of the test wells to generate assay results, wherein the interrogating step comprises the steps of:
      (i) directing excitation light through a bottom surface of said plate; and
      (ii) detecting where targets bound on said probe arrays.

23. The method of claim 1 wherein the interrogating step comprises determining the on-or off-rates of binding between target molecules in a sample and probes.

24. The method of claim 1 wherein the probe arrays are produced by light-directed probe synthesis.

25. The method as recited in claim 24 wherein said arrays of probes are made by repeating the steps of:
   (a) selectively directing light at said surface to remove photoremovable protecting groups; and
   (b) selectively coupling monomers to said surface.

26. The method of claim 24 wherein the chip plate comprises a contiguous substrate that comprises a contiguous surface and the plurality of probe arrays are attached to the contiguous surface.

27. The method of claim 1 wherein each probe array is about 0.25 $cm^2$.

28. The method of claim 1 wherein each probe array is about 1 $cm^2$.

29. The method of claim 1 wherein the probe arrays comprise leatures of about 100 microns on a side.

30. The method of claim 1 wherein the probe arrays comprise features of about 20 microns on a side.

31. The method of claim 1 wherein the chip plate comprises a contiguous substrate that comprises a contiguous surface and the plurality of probe arrays are attached to the contiguous surface.

* * * * *

UNITED STATES PATENT AND TRADEMARK OFFICE
CERTIFICATE OF CORRECTION

PATENT NO. : 6,720,149 B1
DATED : April 13, 2004
INVENTOR(S) : Rava et al.

It is certified that error appears in the above-identified patent and that said Letters Patent is hereby corrected as shown below:

Column 12,
Line 59, "ofdifferent" should read -- of different --;

Column 13,
Line 14, "moleculcs" should read -- molecules --;
Line 38, "fluorcscein" should read -- fluorescein --;
Line 38, "cyanninc" should read -- cyanine --;
Line 42, "polychroniatic" should read -- polychromatic --;
Line 43, "dirccting ail" should read -- directing an --;
Line 45, "conrolling" should read -- controlling --;

Column 14,
Line 16, "diffcrent" should read -- different --.

Signed and Sealed this

Twenty-first Day of December, 2004

JON W. DUDAS
*Director of the United States Patent and Trademark Office*